(12) United States Patent
Shan et al.

(10) Patent No.: US 7,413,756 B2
(45) Date of Patent: Aug. 19, 2008

(54) PROCESSES OF MAKING NORTH AMERICAN GINSENG FRACTIONS, PRODUCTS CONTAINING THEM, AND USE AS IMMUNOMODULATORS

(75) Inventors: Jacqueline J. Shan, Edmonton (CA); Peter K. T. Pang, Edmonton (CA); Buhan Huang, Edmonton (CA); Lei Ling, Edmonton (CA)

(73) Assignee: fX Life Sciences International GmbH, Zug (CH)

( * ) Notice: Subject to any disclaimer, the term of this patent is extended or adjusted under 35 U.S.C. 154(b) by 367 days.

(21) Appl. No.: 11/114,089

(22) Filed: Apr. 26, 2005

(65) Prior Publication Data

US 2005/0196471 A1    Sep. 8, 2005

Related U.S. Application Data

(62) Division of application No. 10/187,289, filed on Jul. 2, 2002, now Pat. No. 7,067,160, which is a division of application No. 09/581,161, filed as application No. PCT/US98/25724 on Dec. 11, 1998, now Pat. No. 6,432,454.

(60) Provisional application No. 60/069,534, filed on Dec. 12, 1997.

(51) Int. Cl.
*A61K 36/25* (2006.01)
(52) U.S. Cl. .................................... 424/728
(58) Field of Classification Search ........... None
See application file for complete search history.

(56) References Cited

U.S. PATENT DOCUMENTS

| | | | |
|---|---|---|---|
| 4,708,949 A | 11/1987 | Liu | |
| 5,071,839 A | 12/1991 | Liu | |
| 5,318,906 A | 6/1994 | Sakata et al. | |
| 5,776,460 A | 7/1998 | Kim et al. | |
| 6,083,932 A | 7/2000 | Pang et al. | |
| 6,156,291 A | 12/2000 | Pang et al. | |
| 6,555,527 B1 | 4/2003 | Yun et al. | |

FOREIGN PATENT DOCUMENTS

| | | | |
|---|---|---|---|
| JP | 61/109732 | | 5/1986 |
| JP | 02/045499 | | 2/1990 |
| WO | WO 99/30725 | * | 6/1999 |
| WO | WO 00/50054 | | 8/2000 |

OTHER PUBLICATIONS

Liu et al., Yaoxue Xuebao, vol. 23, No. 11, pp. 863-867 (1998).
Yamada et al., Phytother. Res., vol. 9, No. 4, pp. 264-269 (1995).
Sun et al., Planta Med., vol. 58, No. 5, pp. 445-448 (1992).
Fujimoto et al., Chem. Pharm. Bull. vol. 39, No. 2, pp. 521-523 (1991).
Database Biosis, Biosciences Information Service, Sep. 1998, Zhou et al, "A study on water-soluble ginsenosides in American Ginseng", Database accession No. PREV199900048177.

* cited by examiner

*Primary Examiner*—Christopher R. Tate
(74) *Attorney, Agent, or Firm*—Rothwell, Figg, Ernst & Manbeck, P.C.

(57) ABSTRACT

The invention is directed to chemical processes of preparing fractions form North American ginseng (*Panax quinquefolium*) and pharmaceutical compositions containing these fractions. The products of the present invention may be used to stimulate the production of cytokines and/or antibodies, or as therapeutics targeted at conditions characterized by low immunity, such as the common cold, influenza, chronic fatigue syndrome, AIDS and cancer.

11 Claims, 11 Drawing Sheets

PROCESSES OF MAKING NORTH AMERICAN GINSENG FRACTIONS, PRODUCTS CONTAINING THEM, AND USE AS IMMUNOMODULATORS

This Application is a divisional of U.S. Ser. No. 10/187,289, filed Jul. 2, 2002; which is a divisional of Ser. No. 09/581,161 (now Pat. No. 6,432,454), filed Jul. 27, 2000, which is a 371 of PCT/US98/25724, filed Dec. 11, 1998, which claims the benefit of U.S. Provisional Application No. 60/069,534, filed Dec. 12, 1997.

FIELD OF THE INVENTION

This invention relates to chemical processes of making fractions from North American ginseng (*Panax quinquefolium*) and compositions containing these fractions. The products of the present invention may be used to stimulate the production of antibodies, or as therapeutics targeted at conditions characterized by low immunity, such as the common cold, influenza, chronic fatigue syndrome, AIDS, cancer, etc. The products of the present invention may also be used as a supplement for cancer patients undergoing chemotherapy or radiation therapy, which is known to cause serious suppression of the immune system.

BACKGROUND OF THE INVENTION

For hundreds of years, the use of certain non-toxic agents such as herbal compounds has been widely accepted for a variety of physiological conditions, especially in the Orient. *Panax ginseng* C. A. Meyer is the best known traditional Chinese medicine. The important pharmacological activities of ginseng extracts, alone or in combination with other drugs, include alleviation of renal impairment, inhibition of carcinogenesis and prevention of stress. There are also a number of reports on the influence of ginseng on the immunological responsiveness of the individual. Some immunomodulatory properties that have been reported include enhancement of host resistance against infection, anti-inflammatory effect, inhibition of tumor growth, as well as modulation of some basic immune function at the cellular level. American ginseng, *Panax quinquefolium*, is another specie of ginseng which has gained popularity as a health supplement having many beneficial health effects. Several groups of scientists have attempted to isolate and elucidate the structure of the polysaccharides present in ginseng. Some of the polysaccharides have been demonstrated to be active in modulating the immune system.

A series of studies on the isolation, characterization, and biological evaluation of ginseng polysaccharides was carried out by Tomoda's group in Kyoritsu College of Pharmacy, Japan. In one set of studies, ginseng polysaccharides were fractionated based on their acidity. Two acidic polysaccharides having immunological activities have been isolated from root of Korean ginseng (*Panax ginseng*)[1,2]. The sliced roots were extracted with hot water. The extract was treated with cetyltrimethylammonium bromide (CTAB) in the presence of sodium sulfate. The precipitate was separated, dialyzed, and applied to a Sephadex G-25 column, DEAE-Sephacel (Pharmacia) column to give two pure polysaccharides, which were designated as ginsenan PA and ginsenan PB. Gel chromatography on Toyopearl HW-55F gave the values of $1.6 \times 10^5$ and $5.5 \times 10^4$ for the molecular weight of ginsenan PA and ginsenan PB, respectively. Quantitative analyses showed that ginsenan PA contained 21.3% arabinose, 53.4% galactose, 2.0% rhamnose, 16.0% galacturonic acid and 2.7% glucuronic acid. The molar ratio of these component sugars was 11:22:1:6:1. Ginsenan PB contained 11.0% arabinose, 32.2% galactose, 8.1% rhamnose, 39.9% galacturonic acid, and 5.0% glucuronic acid. The molar ratio was 3:7:2:8:1. Both polysaccharides showed marked reticuloendothelial system-potentiating activity in a carbon clearance test, and pronounced anti-complementary activity and alkaline phosphatase-inducing activity in a dose dependent manner.

In another study[3], an additional two polysaccharides were isolated from the supernatant of the above extract treated with CTAB, i.e., the supernatant was poured into ethanol. The precipitate was separated and applied to columns of DEAE-Sephadex A-25 and Sephadex G-25 to give another two pure polysaccharides, designated S-IA and S-IIA. Gel chromatography on Toyopearl HW-55F gave the values of $5.6 \times 10^4$ and $1.0 \times 10^5$ for the molecular weight of S-IA and S-IIA respectively. Ginsenan S-IA contains 42.3% arabinose, 50.8% galactose and 6.9% galacturonic acid with the molar ratio of 8:8:1. Ginsenan S-IIA is composed of 42.0% L-arabinose, 32.6% galactose, 6.2% glucose, and 19.2% galacturonic acid. The molar ratio is 15:10:2:5.

Several polysaccharide fractions from leaves and roots of *Panax ginseng* have been separated by Yamada's group in the Oriental Medicine Research Center of the Kitasato Institute, Japan. The chemical properties and biological activities were investigated and compared.[4]

Ginseng roots and leaves from China, after treated with ethanol to remove their ginsenosides, were extracted with water, and the residue were extracted with 0.5 M NaOH to give water-soluble and alkaline soluble polysaccharide fractons (designated as GR-2 and GL-2 for the water-soluble fractions and GRA-2 and GLA-2 for the alkaline-soluble fractions, respectively). Based on the acidity of the component polysaccharides, all fractions were further fractionated into strongly acidic (designated as GR-3, GL-3, GRA-3, and GLA-3), weakly acidic (designated as GR-4, GL4, GRA-4, and GLA-4), and neutral polysaccharide fractions (designated as GR-5, GL-5, GRA-5, and GLA-5), by treatment with cetyltrimethylammonium. The roots contained larger amount of polysaccharide than the leaves. The strongly acidic polysaccharide fractions from the roots had a high content of uronic acid, even higher than 50%. Similar component sugars were detected from all fractions. They were rhamnose, arabinose, galactose, glucose, galacturonic acid, and glucuronic acid. Galacturonic acid was the main uronic acid component.

The fraction with highest anti-complementary activity, GL-3, was further fractionated with columns of DEAE-Sephadex, Sepharose CL-6B, DEAE Toyopearl, and ethanol precipitation to give fractions designated as GL-PI through GL-PIV.[5] All fractions contained 32-44% uronic acid. Fraction PI had the highest molecular weight of 50,000. PI and PII consisted mainly of Rha, Gal, and GalA, and PIII contained Fuc in addition, whereas PIV consisted of Gal, Glc, and GalA. A detailed structural determination was performed.

An anti-ulcer pectic polysaccharide (GL-BIII) was isolated from weakly acidic polysaccharide fraction GL4 by chromatography on DEAE Sepharose CL-6B and Sepharose CL-6B. It was mainly composed of Rha, Ara, Man, Gal, Glc, GalA, and GlcA in the molar ratio of 3:4:2:10:1:7:4. Detailed structural determination was performed.[6]

Another macrophage Fc receptor expression-enhancing polysaccharide (GL4II2) was separated from GL-4 by anion-exchange chromatography on DEAE-Sepharose CL-6B. Chemical analysis showed that the sample contained 65% total carbohydrate and 33.7% uronic acid. The composition analysis and structural determination were performed.[7]

Another *Panax ginseng* extract with anticomplementary activity, G-115, was studied by the same group.[8] G-115 was fractionated in order to characterize the active substances for anticomplementary and mitogenic activities. The most potent anticomplementary activity was observed in the crude polysaccharide fraction, G-115G, whereas the water-soluble dialyzable fraction, G-115E, showed the most potent mitogenic activity. G-115G was further purified by precipitation with cetyltrimethylammonium bromide, anion-exchange chromatography on DEAE-Sepharose and gel filtration on Sepharose CL-4B, and a major potent anticomplementary polysaccharide, G-115I1-IIa-2-3 was obtained. This polysaccharide was homogeneous. Its molecular weight was estimated to be $3.68 \times 10^5$. It consisted mainly of arabinose, galactose and glucose in addition to small amounts of galacturonic acid, glucuronic acid and rhamnose.

Ginseng polysaccharides were isolated from Korean, Chinese, and Japanese ginseng by Hikino's group at the Pharmaceutical Institute, Tohoku University, Japan. The hypoglycemic activities of the ginseng polysaccharides have been tested. The composition and some structure feature have been elucidated.[9-14]

Three polysaccharides, quinquefolans A through C, were isolated from American ginseng.[14] Their molecular weights were estimated to be higher than $2.0 \times 10^6$ by gel chromatography over Sephacryl S-500. The neutral sugar components were mannose and glucose (molar ratio, 1.0:2.3) for quinquefolan A, mannose and glucose (1.0:5.5) for quinquefolan B, and xylose for quinquefolan C. The acidic sugar components in quinquefolans A through C were found to be 10.8, 11.7, and 7.1% respectively. The content of peptide moieties in these glycans was 2.7, 2.9, and 2.3% for quinquefolans A through C respectively. All of these polysaccharides showed hypoglycemic effects in normal and alloxan-reduced hypoglycemic mice.

An acidic polysaccharide with the molecular weight of 150,000, called ginsan, was isolated from *Panax ginseng* by a research group at the Laboratory of Immunology, Korean Cancer Center Hospital, Seoul, Korea.[15] This polysaccharide was composed of 3.7% protein and 47.1% hexose (glucose and galactose) and 43.1% uronic acid (galacturonic acid). Ginsan induced the proliferation of T cells and B cells and generated lymphokine activated killer cells from both natural killer and T cells through endogenously produced multiple cytokines.[16]

Miao et al. from Northeast Normal University of China has isolated polysaccharides from American ginseng. The purification and structural analysis were performed.[17]

The biological activities of polysaccharides from American ginseng have been investigated by a research group in Norman Bethune University of Medical Science.[18, 19] They found that polysaccharides from American ginseng (PPQ) enhanced lymphocyte transformation. The effect of polysaccharide from *Panax quinquefolium* (PPQ-1) on cytokine production from murine spleen lymphocyte in vitro was studied. The data suggest that PPQ-1 regulates immune function.

SUMMARY OF THE INVENTION

The present inventors have found that certain American ginseng extracts have immunoregulating properties. CVT-E002, and purified fractions $PQ_2$ and $PQ_{223}$ therefrom, specifically stimulates murine spleen cells to proliferate B cells, which subsequently produce a large amount of antibody. The fractions also increase serum immunoglobulin (e.g., total IgG) levels and stimulate macrophages to produce IL-1, IL-6 and TNF-α. These fractions may be used for the prevention or treatment of general infection and other immune deficiency associated diseases.

Therefore, the present invention is directed to processes of preparing ginseng fractions $PQ_2$, $PQ_{223}$ and CVT-E002 from samples of American ginseng.

Specifically, a process of preparing ginseng fraction $PQ_2$ comprises:
  combining American ginseng with a first solvent comprising an alcohol and heating the resulting solution at a temperature of about 80-100° C. for a time period of about 2-4 hours to produce a first ginseng solution;
  thereafter separating the first ginseng solution to produce an alcohol/ginseng solution and a first ginseng residue;
  thereafter combining the first ginseng residue with water and heating the resulting solution at a temperature of about 80-100° C. for a time period of about 2-4 hours to produce a ginseng residue solution;
  thereafter separating the ginseng residue solution to produce a second ginseng residue and a first aqueous extract solution containing a first ginseng extract;
  providing a second aqueous extract solution which comprises at least a part of the first ginseng extract, wherein in the second aqueous extract solution the proportion of the first ginseng extract to water is about 1:18 to 1:22;
  thereafter combining the second aqueous extract solution with a second solvent comprising an alcohol, wherein the proportion of the second solvent to water is about 1:1 to 3:5, to produce a first precipitate and a first supernatant;
  thereafter combining the first supernatant produced in the previous step with a third solvent comprising an alcohol, wherein the proportion of the third solvent to first supernatant is about 3:2 to 3:1, to produce a second precipitate and a second supernatant; and
  isolating the second precipitate to produce ginseng fraction $PQ_2$.

A process of preparing ginseng fraction $PQ_{223}$ comprises:
  providing ginseng fraction $PQ_2$, as described above;
  fractionating the ginseng fraction $PQ_2$ to produce a first elution fraction and a second elution fraction wherein the first elution fraction corresponds to a carbohydrate peak observed between 35 and 50 ml of elution volume and the second elution fraction corresponds to a carbohydrate peak observed between 50 and 85 ml of elution volume, as determined by gel filtration chromatography using the following materials:
    (1) a chromatographic column containing a matrix of a spherical cross-linked co-polymer of allyl dextran and N,N'-methylenebisacrylamide, having a bed dimension of 16×600 mm, a bed volume of 120 ml, and a fractionation range (MW) of 5000 to 250,000 for globular proteins and 1000 to 80,000 for dextrans, and
    (2) an elution buffer of Tris-HCl containing 0.1 N HCl and 0.3 M NaCl at a pH of 7.0; and
  isolating and combining the first elution fraction and the second elution fraction to produce ginseng fraction $PQ_{223}$.

A process of preparing ginseng fraction CVT-E002 comprises:
  combining American ginseng with a first solvent comprising an alcohol in a proportion of about 7-9 ml of first solvent per gram of ginseng and heating the resulting solution at a temperature of about 80-100° C. for a time period of about 2-4 hours, to produce a first ginseng solution;

thereafter separating the first ginseng solution to produce an alcohol/ginseng solution and a first ginseng residue;

thereafter combining the first ginseng residue with water in a proportion of about 7-9 ml of water per gram of ginseng residue and heating the ginseng residue solution at a temperature of about 80-100° C. for a time period of about 2-4 hours, to produce a ginseng residue solution;

thereafter separating the ginseng residue solution to produce a second ginseng residue and an aqueous extract solution containing a ginseng extract; and drying the aqueous extract solution to produce ginseng fraction CVT-E002.

The present invention also includes ginseng fractions $PQ_2$, $PQ_{223}$ and CVT-E002, which are prepared according to the processes described above.

The invention further includes ginseng fractions having specific carbohydrate contents.

A first ginseng fraction has a carbohydrate content which comprises about 2-6 mol % rhamnose, about 41-49 mol % galacturonic acid, about 12-18 mol % glucose, about 16-22 mol % galactose and about 12-19 mol % arabinose.

A second ginseng fraction has a carbohydrate content which comprises about 3-8 mol % rhamnose, about 36-44 mol % galacturonic acid, about 2-7 mol % glucose, about 25-33 mol % galactose and about 17-25 mol % arabinose.

A third ginseng fraction has a carbohydrate content which comprises about 0.5-5 mol % rhamnose, about 11-22 mol % galacturonic acid, about 40-60 mol % glucose, about 10-19 mol % galactose and about 11-19 mol % arabinose.

The invention also includes pharmaceutical compositions, comprising the ginseng fractions of the invention, in combination with a pharmaceutically acceptable carrier.

The invention further includes the use of a ginseng fraction according to the invention, alone or in combination with another medicament, in the preparation of a pharmaceutical composition suitable for treating a condition characterized by low immunity.

The invention also includes the use of a ginseng fraction of the invention to stimulate the production of IL-1, IL-6 and/or TNF-α in cells.

The invention further includes the use of a ginseng fraction according to the invention to stimulate the in vitro or in vivo production of immunoglobulins.

Also included is the use of a ginseng fraction according to the invention to activate B-lymphocyte proliferation and antibody production therefrom.

The invention also includes a method of treating a condition characterized by low immunity in a patient in need thereof, comprising administering to the patient a condition treating effective amount of a ginseng fraction according to the invention.

DETAILED DESCRIPTION OF THE INVENTION

Figure 1:
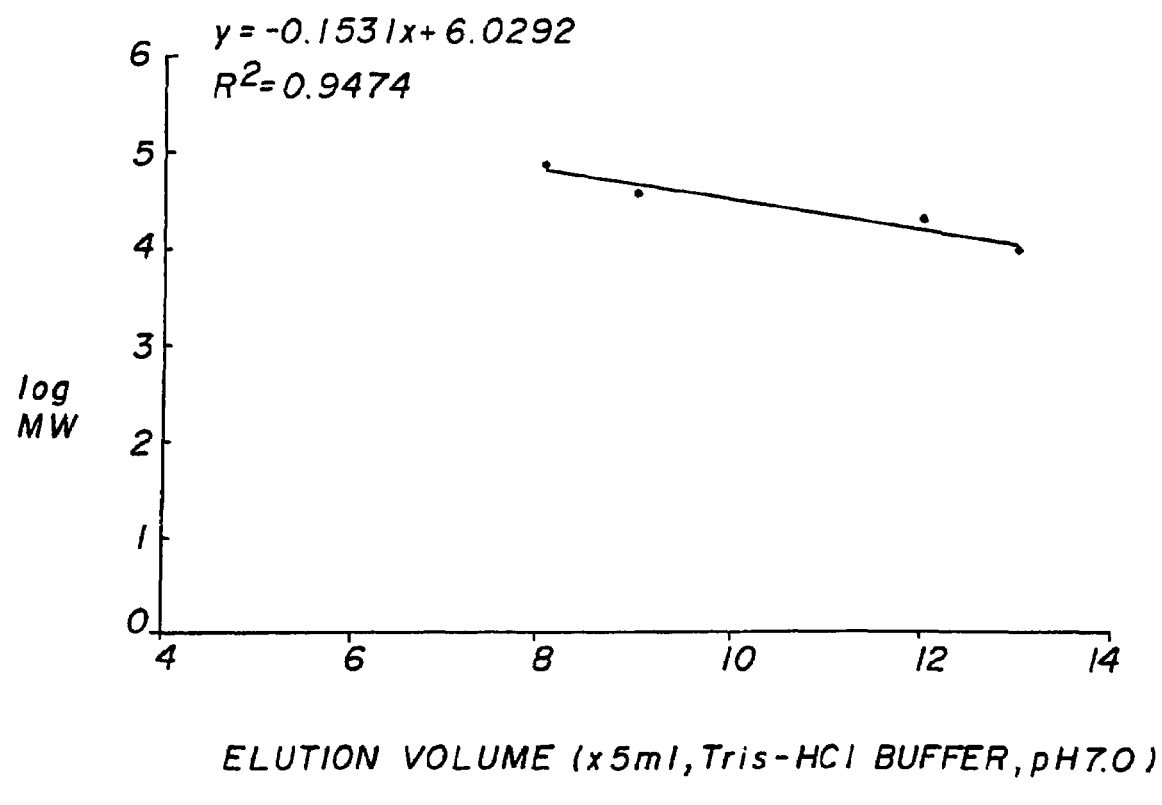
FIG. 1 shows a plot of elution volume against log molecular weight for standard dextran samples eluted on a chromatographic column.
Figure 2:
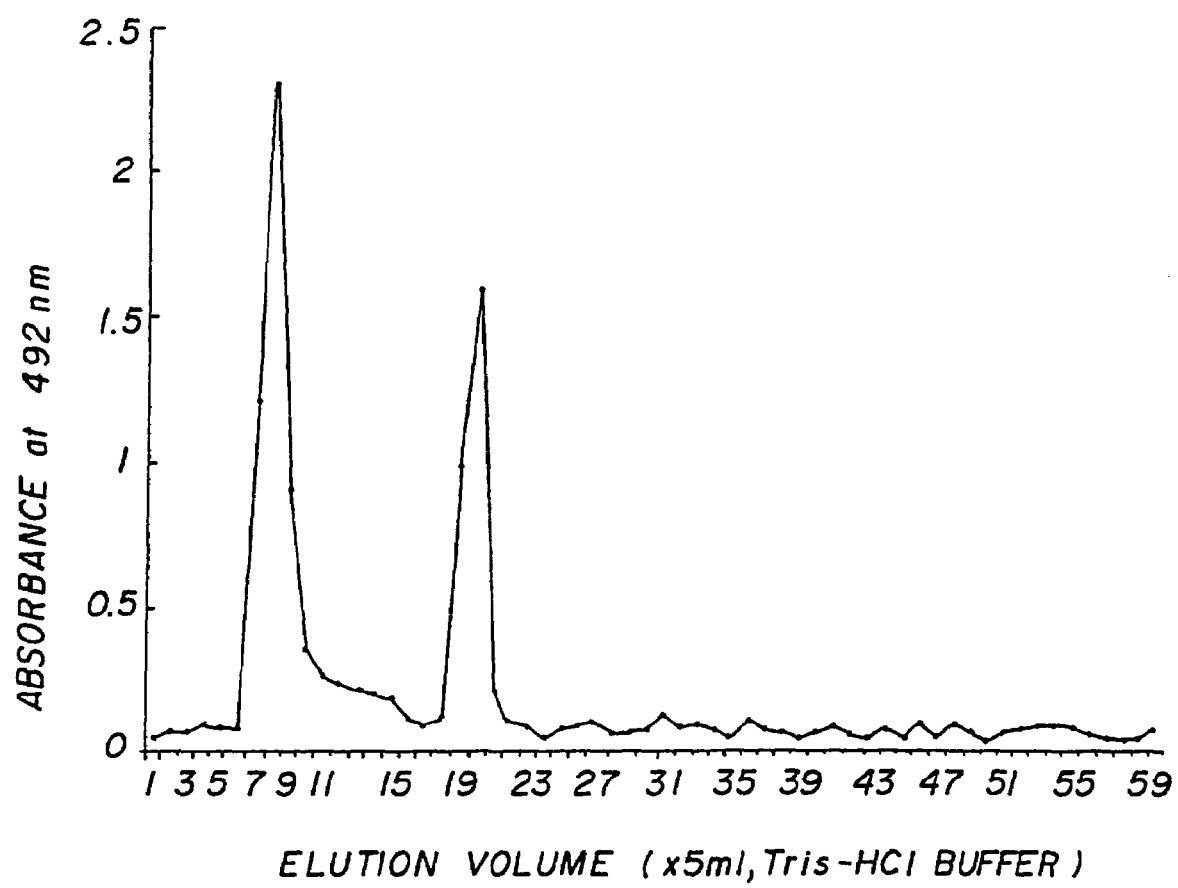
FIG. 2 shows a chromatogram of ginseng fraction CVT-E002.
Figure 3:
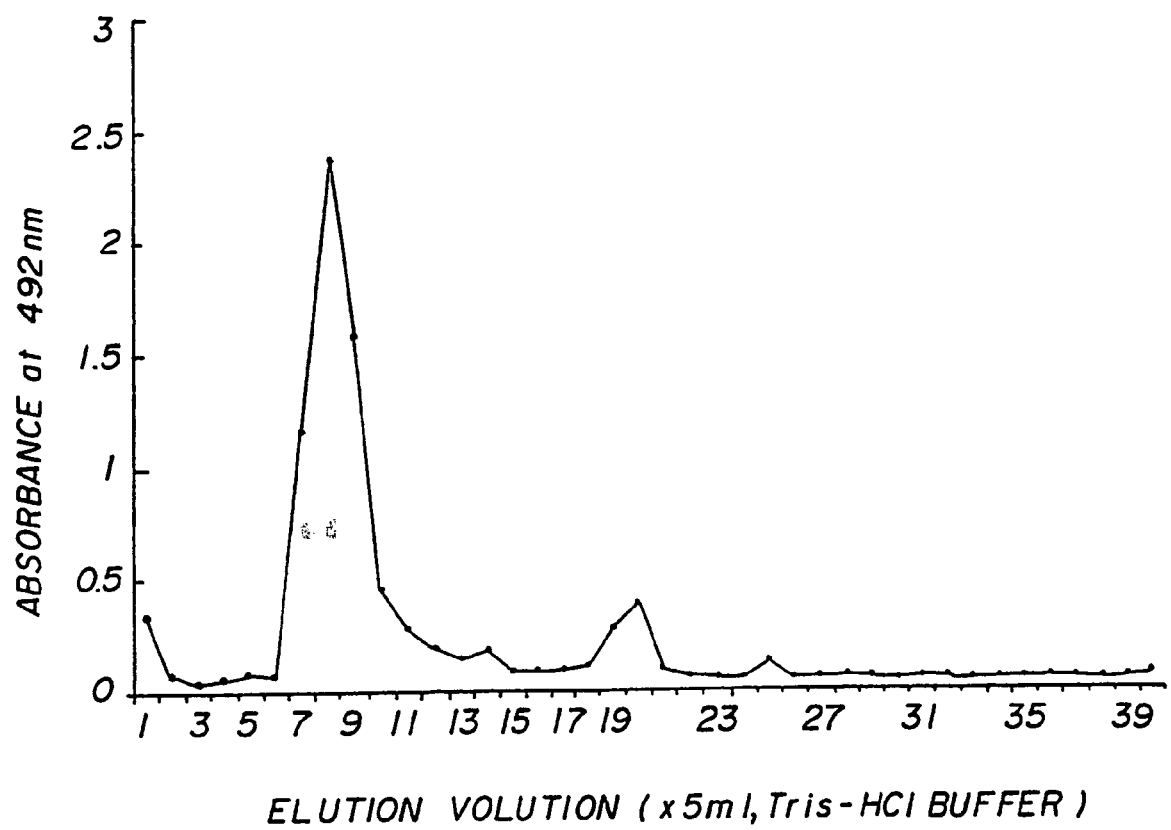
FIG. 3 shows a chromatogram of ginseng fraction $PQ_1$.

A process of preparing ginseng fraction $PQ_2$ comprises:

(a) combining American ginseng with a first solvent comprising an alcohol and heating the resulting solution at a temperature of about 80-100° C. for a time period of about 2-4 hours to produce a first ginseng solution;

(b) thereafter separating the first ginseng solution to produce an alcohol/ginseng solution and a first ginseng residue;

(c) thereafter combining the first ginseng residue with water and heating the resulting solution at a temperature of about 80-100° C. for a time period of about 2-4 hours to produce a ginseng residue solution;

(d) thereafter separating the ginseng residue solution to produce a second ginseng residue and a first aqueous extract solution containing a first ginseng extract;

(e) providing a second aqueous extract solution which comprises at least a part of the first ginseng extract, wherein in the second aqueous extract solution the proportion of the first ginseng extract to water is about 1:18 to 1:22;

(f) thereafter combining the second aqueous extract solution with a second solvent comprising an alcohol, wherein the proportion of the second solvent to water is about 1:1 to 3:5, to produce a first precipitate and a first supernatant;

(g) thereafter combining the first supernatant produced in step (f) with a third solvent comprising an alcohol, wherein the proportion of the third solvent to first supernatant is about 3:2 to 3:1, to produce a second precipitate and a second supernatant; and (h) isolating the second precipitate to produce ginseng fraction $PQ_2$.

The alcohol in each of the first solvent, second solvent and third solvent comprises an alcohol which is inert to the ginseng and is easily separated from the desired product. Those of skill in the art would readily be able to select alcohols which meet these requirements. Preferably the alcohol in each case independently comprises a saturated or unsaturated $C_1$-$C_6$ alcohol. More preferably, the alcohol in each case independently comprises ethanol or methanol.

In each of steps (a) and (c), it is preferred that the resulting solution is heated for a time period of about 3 hours. It is also preferred that in step (a) the first solvent and the ginseng are combined in a proportion of about 7-9 ml of first solvent per gram of ginseng, most preferred about 8 ml of first solvent per gram of ginseng. In step (c), it is preferred that the water and the first ginseng residue are combined in a proportion of about 7-9 ml of water per gram of ginseng residue, most preferred about 8 ml of water per gram of ginseng residue.

Directly following step (d) in the process recited above, the first ginseng extract may optionally be concentrated. This may be accomplished in any way according to procedures well known to those of skill in the art. For example, the first aqueous solution containing the first ginseng extract may be centrifuged (e.g., at a speed of 2500 to 10,000 rpm for about 5-15 minutes). The first aqueous solution may also be filtered. Alternatively or in addition to concentrating the first ginseng extract, the first ginseng extract may be freeze dried for later use.

In step (e), the second aqueous extract solution comprises at least a part of the first ginseng extract. It is important that the ratio of first ginseng extract to water in the second aqueous extract solution be about 1:18 to 1:22, more preferably about 1:20. This may be achieved in any of a number of ways. If the first ginseng extract is concentrated and/or freeze dried following step (d), as described above, water should be added to the first ginseng extract to achieve the desired ratio. Alternatively, a part of the first aqueous extract solution, or the entire first aqueous extract solution, may be used in the second aqueous extract solution. If needed, additional water may be added to achieve the desired ratio. The use of at least a part of the first aqueous extract solution which contains the desired amount of first ginseng extract would avoid the need to conduct additional concentrating or freeze drying steps between steps (d) and (e).

In step (f), it is preferred that the proportion of the second solvent to water is about 3:4.

In step (g), it is preferred that the proportion of the third solvent to first supernatant is about 2:1.

A process of preparing ginseng fraction $PQ_{223}$ comprises:
(a) providing ginseng fraction $PQ_2$, produced according to the process described above;
(b) fractionating the ginseng fraction $PQ_2$ to produce a first elution fraction and a second elution fraction, wherein the first elution fraction corresponds to a carbohydrate peak observed between 35 and 50 ml of elution volume and the second elution fraction corresponds to a carbohydrate peak observed between 50 and 85 ml of elution volume, as determined by gel filtration chromatography using the following materials:
  (1) a chromatographic column containing a matrix of a spherical cross-linked co-polymer of allyl dextran and N,N'-methylenebisacrylamide, having a bed dimension of 16×600 mm, a bed volume of 120 ml, and a fractionation range (MW) of 5000 to 250,000 for globular proteins and 1000 to 80,000 for dextrans, and
  (2) an elution buffer of Tris-HCl containing 0.1 N HCl and 0.3 M NaCl at a pH of 7.0; and
(c) isolating and combining the first elution fraction and the second elution fraction to produce ginseng fraction $PQ_{223}$.

The first elution fraction is also known as $PQ_2A$, and the second elution fraction is also known as $PQ_2B$. These elution fractions may be isoated separately. Additionally, the same process as noted above may be used to produce additional elution fractions $PQ_2C$ (which corresponds to a carbohydrate peak observed between 95 and 110 ml of elution volume, and $PQ_2D$ (which corresponds to a carbohydrate peak observed between 120 and 250 ml of elution volume). Each of these fractions may also be separately isolated. In addition, compositions besides $PQ_{223}$ which comprise two or more of fractions $PQ_2A$ through $PQ_2D$ may be also made.

It is preferred that ginseng fraction $PQ_2$ is fractionated using gel filtration chromatography. However, any other types of fractionation known to the skilled artisan are suitable.

The procedure for performing gel filtration chromatography is well known by those of ordinary skill in the art, following manufacturer's recommendations as to flow rate, sample volume and temperature at which the procedure should be performed. Variance of these factors within the manufacturer's specifications does not significantly affect the results of the chromatographic run.

Determination of carbohydrate content may be made by any procedure known in the art. It is preferred that a microtiter plate assay be conducted for the determination of the carbohydrate composition of the fraction. Such an assay is well known to those of skill in the art. See, for example, Dubois et al. *Anal. Chem.* 28: 350-56 (1956), hereby incorporated by reference. Absorbance of the sample provided according to the microtiter plate assay is preferably conducted at 492 nm.

A process of preparing ginseng fraction CVT-E002 comprises:
(a) combining American ginseng with a first solvent comprising an alcohol in a proportion of about 7-9 ml of first solvent per gram of ginseng and heating the resulting solution at a temperature of about 80-100° C. for a time period of about 2-4 hours, to produce a first ginseng solution;
(b) thereafter separating the first ginseng solution to produce an alcohol/ginseng solution and a first ginseng residue;
(c) thereafter combining the first ginseng residue with water in a proportion of about 7-9 ml of water per gram of ginseng residue and heating the ginseng residue solution at a temperature of about 80-100° C. for a time period of about 2-4 hours, to produce a ginseng residue solution;
(d) thereafter separating the ginseng residue solution to produce a second ginseng residue and an aqueous extract solution containing a ginseng extract; arid
(e) drying or concentrating the aqueous extract solution to produce ginseng fraction CVT-E002.

The alcohol in the first solvent comprises an alcohol which is inert to the ginseng and is easily separated from the desired product. Those of skill in the art would readily be able to select alcohols which meet these requirements. Preferably the alcohol comprises a saturated or unsaturated $C_1$-$C_6$ alcohol. More preferably, the alcohol comprises ethanol or methanol.

It is preferred that in step (a) the first solvent and the sample are combined in a proportion of about 8 ml of first solvent per gram of sample. It is also preferred that in step (c) the water and the first ginseng residue are combined in a proportion of about 8 ml of water per gram of ginseng residue.

In steps (a) and (c), it is preferred that the first ginseng solution is heated for a time period of about 3 hours.

The invention also includes several ginseng fractions.

A first ginseng fraction has a carbohydrate content which comprises about 2-6 mol % rhamnose, about 41-49 mol % galacturonic acid, about 12-18 mol % glucose, about 16-22 mol % galactose and about 12-19 mol % arabinose. Preferably, the carbohydrate content comprises about 3-5 mol % rhamnose, about 43-47 mol % galacturonic acid, about 14-16 mol % glucose, about 18-20 mol % galactose and about 14-17 mol % arabinose. Most preferably, the carbohydrate content comprises about 4 mol % rhamnose, about 45 mol % galacturonic acid, about 15 mol % glucose, about 19 mol % galactose and about 15 mol % arabinose.

A second ginseng fraction in accordance with the invention has a carbohydrate content which comprises about 3-8 mol % rhamnose, about 36-44 mol % galacturonic acid, about 2-7 mol % glucose, about 25-33 mol % galactose and about 17-25 mol % arabinose. Preferably, the carbohydrate content comprises about 4-7 mol % rhamnose, about 37-42 mol % galacturonic acid, about 3-6 mol % glucose, about 27-32 mol % galactose and about 19-24 mol % arabinose. Most preferably, the carbohydrate content comprises about 5 mol % rhamnose, about 39 mol % galacturonic acid, about 4 mol % glucose, about 29 mol % galactose and about 21 mol % arabinose.

A third ginseng fraction according to the invention has a carbohydrate content which comprises about 0.5-5 mol % rhamnose, about 11-22 mol % galacturonic acid, about 40-60 mol % glucose, about 10-19 mol % galactose and about 11-19 mol % arabinose. Preferably, the carbohydrate content comprises about 1-3 mol % rhamnose, about 13-20 mol % galacturonic acid, about 42-57 mol % glucose, about 12-17 mol % galactose and about 13-17 mol % arabinose.

The invention also includes pharmaceutical compositions, comprising any of the ginseng fractions according to the invention in combination with a pharmaceutically acceptable carrier. Those of skill in the art are familiar with any pharmaceutically acceptable carrier which would be useful in this regard, and therefore the procedure for making pharmaceutical compositions in accordance with the invention will not be discussed in detail. Suitably, the pharmaceutical compositions may be in the form of tablets, capsules, liquids, lozenges, lotions or suppositories.

The invention includes the use of a ginseng fraction according to the invention in the preparation of a pharmaceutical composition suitable for treating a condition characterized by low immunity, such as common cold, influenza, chronic fatigue syndrome, AIDS and cancer. The ginseng fraction may be used alone or in combination with another medicament. The ginseng fractions of the invention are especially suitable for co-administration with a chemotherapeutic agent or as a supplement to radiation therapy, since cancer patients are known to have serious suppression of the immune system.

The invention also includes a method of treating a condition characterized by low immunity in a patient in need thereof, comprising administering to the patient a condition treating effective amount of a ginseng fraction according to the invention. Preferably, the condition is selected from the group consisting of common cold, influenza, chronic fatigue syndrome, AIDS and cancer. Dosages of ginseng fractions in accordance with the invention depend upon the particular condition to be treated, as well as the age, sex and general health condition of the patient. However, suitable dosages may be found in the range between 1 and 5000 mg/kg body weight per day, in between 1 and 10 daily doses. The ginseng fractions may be administered orally, via injection or infusion, topically, nasally, ocularly, vaginally or rectally.

The invention will now be further elucidated by the following Examples.

EXAMPLE 1

A First Process for Preparing Fraction CVT-E002 and Purifying This Fraction

American ginseng root was chemically extracted and purified sequentially to give fractions CVT-E002 and CVT-E002. An amount of CVT-E002 was further purified to give fractions $G_1$, $G_2$ and $G_3$. The detailed description of the procedure is as follows.

500 grams of dried ground root of ginseng was extracted with 4 liters of 85% ethanol or 3 liters of 90% methanol on a water bath at 80-85° C. while stirring for 3 hours and filtered to give an alcohol solution and residue. The alcohol solution was concentrated and spray dried to give a product of total saponins (CVT-E001). The residue was extracted with 4 liters of water on a water bath at 95-100° C. while stirring for 3 hours. The extract was filtered through a muslin bag and centrifuged to give an aqueous solution containing CVT-E002, and the remaining residue was discarded.

A portion of the aqueous solution was used for further purification, and an equal volume of 95% ethanol was added to the aqueous solution, which caused precipitation. The precipitate was centrifuged and lyophilized to give the fraction $G_1$. The supernatant was reduced in volume by evaporation. An equal volume of 95% ethanol was added to give the next precipitate, $G_2$, and the remaining supernatant was removed with ethanol and lyophilized to produce a powder, $G_3$.

The further purification of $G_2$ was conducted as follows. Two grams of $G_2$ were dissolved in 80 ml of water and dialyzed against 3 volumes of water in a Sigma D-7884 dialysis tubing with a 1200 molecular weight cut-off. The dialysis was done at 4° C. for 72 hours, collecting dialysate twice every 24 hours. The resulting dialysate was concentrated to 15 ml, then precipitated with an equal volume of methanol. The precipitate was dissolved in water and lyophilized to yield a powder, $G_{22}$.

The further purification of $G_{22}$ was conducted as follows. 1.5 grams of $G_{22}$ were dissolved in 60 ml water and then dialyzed against 600 mls of water in a Fisher Spectral/Por molecularporous membrane tubing with a 1000 molecular weight cut-off at 4° C. The first dialysate collected after 24 hours was concentrated to 15 mls using an evaporator and then lyophilized. The resulting dried powder was referred to as $G_{221}$. In a similar manner, a second batch of dialysate was collected after 48 hours and referred to as $G_{222}$. The retentate was concentrated and lyophilized to give a powder called $G_{223}$.

EXAMPLE 2

A Second Process for Preparing Fraction CVT-E002 and Purifying This Fraction

An alternative process for preparing ginseng fraction CVT-E002 according to the invention is as follows.

1000 grams of dried ground root of American ginseng was extracted with 8 liters of 85% ethanol on a water bath at 95-100° C. while stirring for 3 hours and filtered to give an alcohol solution and residue. The residue was combined with water (1:8) on a hot water bath with continuing agitation for 3 hours. After cooling to room temperature, the mixture was filtered. The filtrate was centrifuged at 5000 rpm for 10 min. The supernatant was concentrated and freeze dried to give extract CVT-E002. The amount of CVT-E002 produced by this method is approximately the same as produced according to Example 1, i.e., about 10% of the weight of the original raw ginseng.

A portion of CVT-E002 was further fractionated as follows. 1600 ml of 95% ethanol was added to a solution of 100 grams of CVT-E002 powder in 2000 ml of water. The precipitate was isolated as $PQ_1$. The supernatant was concentrated to 500 ml. Another portion of 95% ethanol (1000 ml) was added to this concentrated solution again to give second precipitate fraction. The precipitate was isolated and freeze dried to give fraction $PQ_2$. The supernatant was concentrated and freeze dried to give $PQ_3$.

EXAMPLE 3

Mitogenic Activity Test

Different fractions of American ginseng at various levels of purification were selected by screening on the basis of their mitogenic activity of lymphocytes in vitro. Though mitogenicity is considered a rather artificial event in relation to the normal events occurring in the immune system in vivo, mitogens provide good indications of possible effector function.

The test method for mitogenic activity is described as follows: Balb/C or C57B1/6J mice were used for the test. Balb/C mice were obtained from the Health Sciences Laboratory Animal Services facility (University of Alberta, Edmonton, Canada). C57B1/6J mice were obtained from the Jackson Laboratory (Bar Harbor, Me.). Mice from 7 to 10 weeks old were age and sex matched for each experiment. Mice were killed by cervical dislocation. Spleens were removed by using aseptic techniques and were crushed between the frosted ends of two glass slides. After washing by centrifugation in Hanks Balanced Salt Solution (HBSS), the cells were suspended in RPMI 1640 medium pH 7.4 (Gibco, Grand Island, N.Y.) containing 10% fetal bovine serum (Flow Labs), 50 mM mercaptoethanol (ICN Pharmaceuticals, Plainview, N.Y.), and penicillin-streptomycin (Gibco). Cultures were set up in triplicate in 96-well flat-bottomed Linbro plates at $1.25 \times 10^6$ cells per ml final concentration. Experimental groups were set up with testing fractions previously filter-sterilized and dissolved in HBSS. Control cultures consisted of a group without mitogen and groups with 20 μg/ml phytohemagglutinin (PHA) or 25 μg/ml lipopolysaccharide (LPS). It is known that PHA specifically stimulates the T-type of spleen cells while LPS stimulates the B-type of spleen cells. The cultures were incubated at 37° C. in a humidified 5% $CO_2$ atmosphere for 72 hours. Four hours before the end of the 72 hour incubation, 1 μCi of tritiated thymidine (New England Nuclear, Boston, Mass.) was added to each well. The cells were harvested with an automated sample harvester (Skatron, Va.) and then incorporated radioactivity was assayed by scintillation counting. The results were calculated as a % of control (mean ±standard deviation, in triplicate).

The different extraction conditions shown in Examples 1 and 2, such as concentration of CVT-E002 in water and the volume of ethanol used for precipitation, affect the further fractionation of the CVT-E002. The products obtained from these two processes were compared for mitogenic activity. The results are shown in the following Tables. Each test was performed in triplicate with three batches.

TABLE 1

Mitogenic activity of $G_1$, $G_2$, and $G_3$ obtained from procedure according to Example 1

| Fractions | Activity (% control) | | |
|---|---|---|---|
| | Batch 1 | Batch 2 | Batch 3 |
| $G_1$ | 4090 ± 1644 | 2845 ± 1318 | 4446 ± 977 |
| $G_2$ | 3015 ± 1284 | 4101 ± 1671 | 3146 ± 318 |
| $G_3$ | 1791 ± 573 | 1735 ± 96 | 365 ± 26 |

TABLE 2

Mitogenic activity of $PQ_1$, $PQ_2$, and $PQ_3$ obtained from procedure according to Example 2

| Fractions | Activity (% control) | | |
|---|---|---|---|
| | Batch 1 | Batch 2 | Batch 3 |
| $PQ_1$ | 2448 ± 454 | 3169 ± 431 | 2492 ± 138 |
| $PQ_2$ | 6427 ± 1609 | 6467 ± 1593 | 7034 ± 1834 |
| $PQ_3$ | 1313 ± 288 | 1522 ± 342 | 1622 ± 222 |

As Tables 1 and 2 indicate, the change in extraction procedure between Examples 1 and 2 correlates with a transfer of biological activity from the $G_1$ fraction to the $PQ_2$ fraction.

EXAMPLE 4

Fractionation of $PQ_2$ and a Process for Preparing Fraction $PQ_{223}$

CVT-E002, $PQ_1$, $PQ_2$ and $PQ_3$ according to Example 2 were further fractionated according to their molecular weight distribution by gel filtration chromatography over a HiPrep 16/60 Sephacryl S-200 high resolution column (Pharmacia Biotech, Cat. No. 17-1166-01), which contains a matrix of a spherical cross-linked co-polymer of allyl dextran and N,N'-methylenebisacrylamide, has a bed dimension of 16×600 mm, a bed volume of 120 ml, and a fractionation range (MW) of 5000 to 250,000 for globular proteins and 1000 to 80,000 for dextrans. Dextran samples (MW=71.4 k, 37.5 k, 19.5 k and 9.5 k) were purchased from Sigma and were used as standard samples. 5 mg of each sample was dissolved in 1 ml of water, loaded onto the column, and eluted with Tris-HCl buffer containing 0.1 N HCl and 0.3 M NaCl, pH 7.0, flow rate 0.3 ml/min and environmental temperature 4° C. A volume of eluate was collected as a number of individual 5 ml portions.

Total carbohydrate content of each individual portion of eluate was tested with a microtiter plate assay for total carbohydrate content. This is a modification of a method described in Dubois et al. *Anal. Chem.* 28: 350-56 (1956). The total carbohydrates in the eluate are derivatized in order to be detectable at a certain absorbance spectrum. D-glucose was used as the standard sample, and other materials used were concentrated sulfuric acid (98%) and 5% phenol. The polystyrene microtiter plates were purchased from SARSTDT (Quebec, Canada). To each well of a microtiter plate, 40 μl of a standard sample solution containing 1 to 10 μg of D-glucose was applied and 40 μl of 5% phenol was added and mixed. 200 μl of concentrated sulfuric acid was then carefully added. After mixing reagent and individual portion of eluate with a multichannel pipette, the plate was incubated under 80° C. for 1 hour. After cooling to room temperature, the absorbance of the sample was measured at 492 nm on a Multiskan microtiter plate reader. The data was saved and the gel filtration chromatography results were plotted using the Microsoft Excel program.

A standard curve was created by running a series of standard dextrans (Sigma) with known molecular weights over the same column (FIG. 1). The chromatograms for CVT-E002 and lots 21 of $PQ_1$, $PQ_2$ and $PQ_3$ are shown in FIGS. 2-5. In each Figure, points on the x-axis show the elution volume in terms of one-fifth of the actual volume. In order to get a true value of elution volume, therefore, the results in the Figures must be multiplied by five.

The gel filtration chromatogram of CVT-E002 (FIG. 2) showed mainly three peaks. The molecular weight for first peak (elution fraction 7-10) was estimated to be 70,000 or higher according to the standard curve (FIG. 1). The molecular weight for the third peak (elution fraction 18-22) was estimated to be about 1,000. A small broad second peak (elution fraction 10-17) was also observed. The ratio of these three peaks was 57.2:8.5:34.4.

The chromatogram of $PQ_1$ (FIG. 3) showed one main peak (elution fraction 7-10), which corresponds to the high molecular weight fraction of CVT-E002, and a minor peak (elution fraction 18-21). The ratio of the two peaks was 86.8:13.2.

Figure 4:
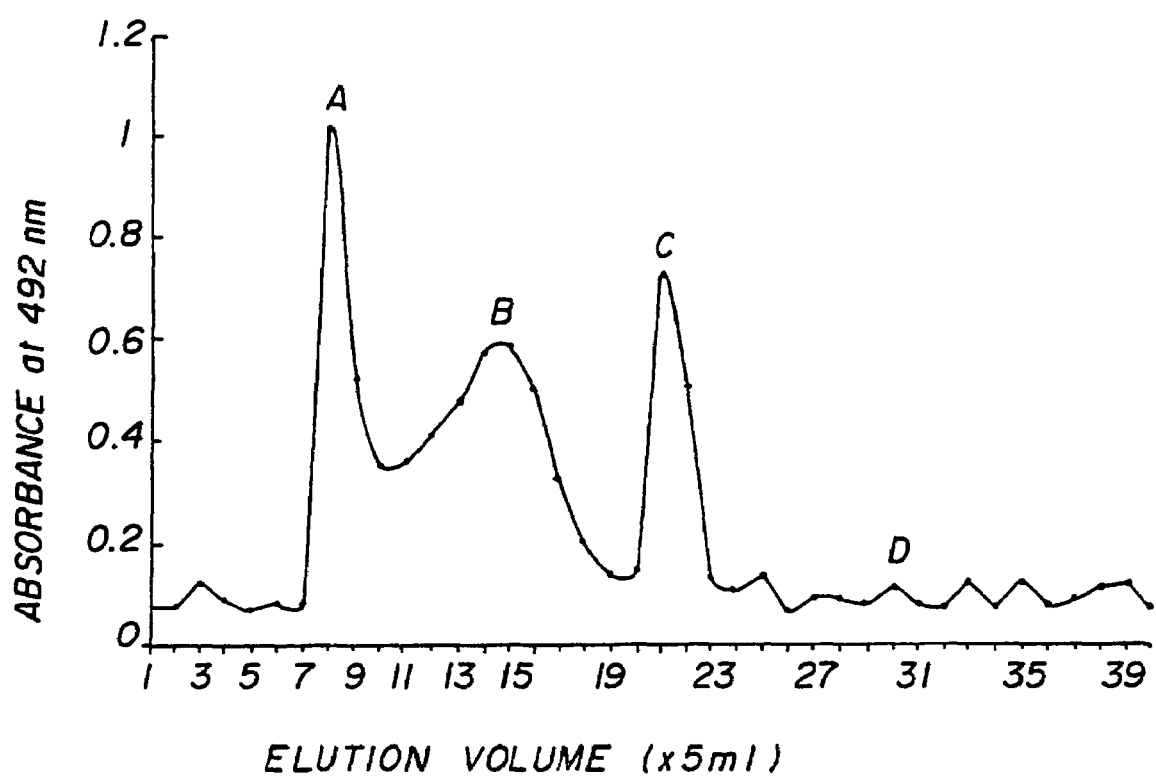
FIG. 4 shows a chromatogram of ginseng fraction $PQ_2$.
Figure 5:
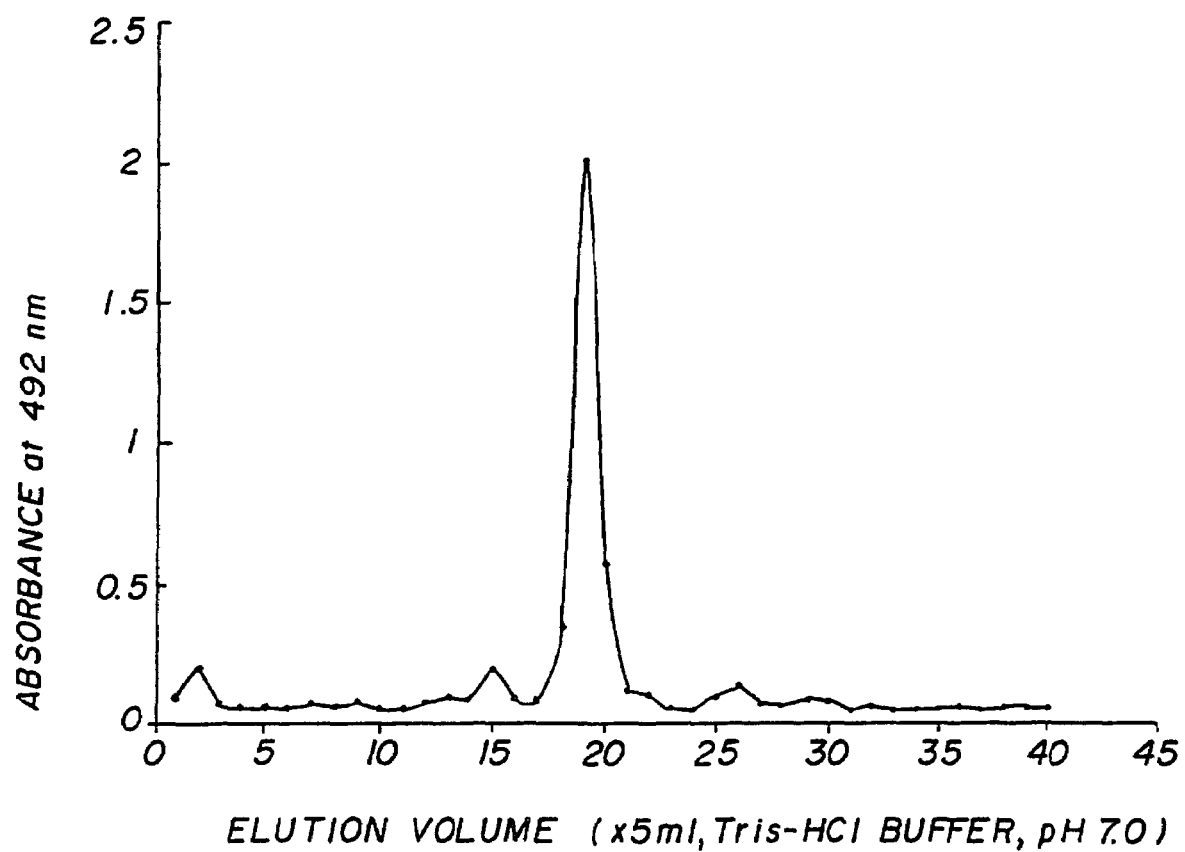
FIG. 5 shows a chromatogram of ginseng fraction $PQ_3$.

The chromatogram of $PQ_2$ (FIG. 4) showed three main peaks. The peak designated A (elution fraction 7-10) and the peak designated C (elution fraction 19-22) correspond to the two main peaks of CVT-E002. Another broad peak, designated B (elution fraction 10-17), was observed between peaks A and C. The molecular weight for this peak was estimated to be about 2,000-60,000. The ratio of the three peaks A-C was 34.1:45.7:20.3. A region of small peaks, designated D (elution fraction 24-50, a portion of which is shown in FIG. 4), was also observed.

The chromatograph of $PQ_3$ (FIG. 5) showed only one main peak (elution fraction 18-21), which corresponded to the low molecular weight fraction of CVT-E002.

Figure 6:
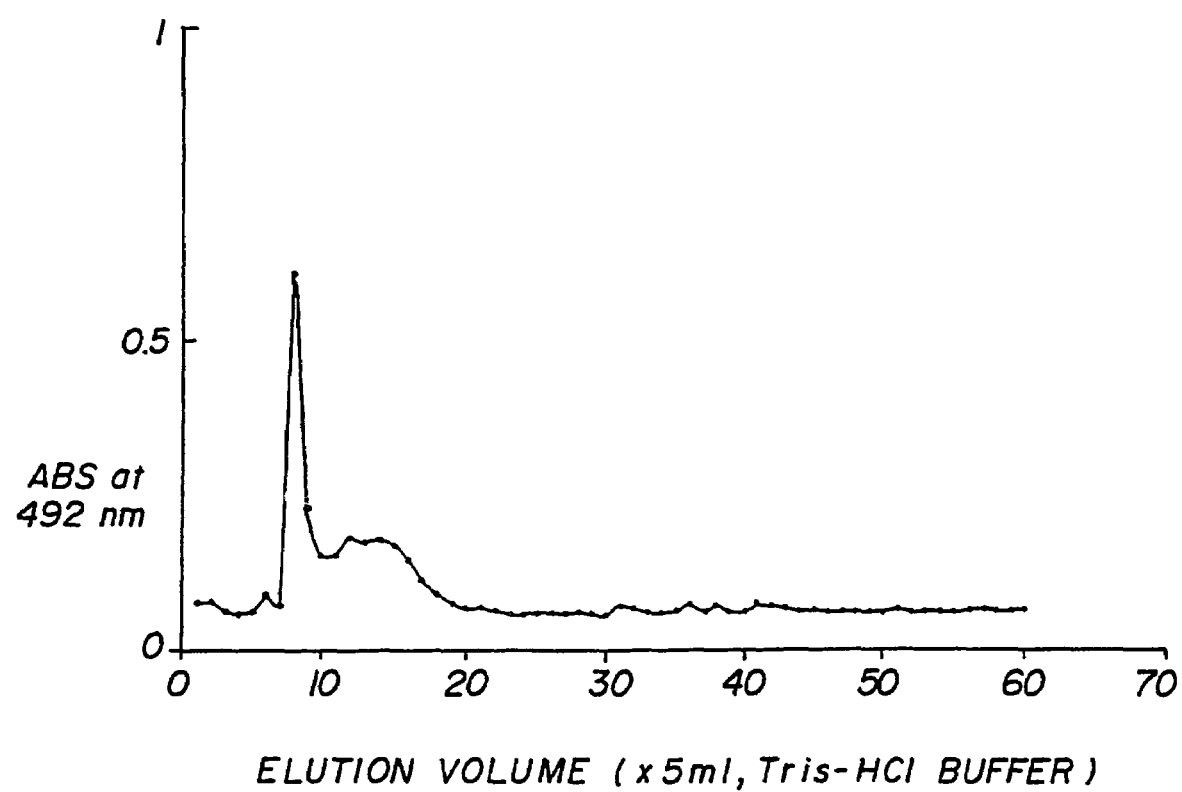
FIG. 6 shows a chromatogram of ginseng fraction $PQ_{223}$.

Fractions A, B, C and D of $PQ_2$ were collected and freeze dried. The dried powders were renamed as $PQ_2A$, $PQ_2B$, $PQ_2C$ and $PQ_2D$, respectively. Fractions A and B were also combined, and the combined fraction was called $PQ_{223}$ (a chromatograph of which is shown in FIG. 6). The mitogenic activity of PQ2A, $PQ_2B$, $PQ_2C$ and $PQ_2D$ were tested and compared with the activity of fractions $PQ_{223}$, $PQ_2$ and CVT-E002. The results are shown in the following Table.

TABLE 3

Mitogenic activity of American ginseng fractions
($^3$H-thymidine incorporation as % of control)

| Sample | Dose (μg/ml) | Activity (% of Control) |
|---|---|---|
| Control | n/a | 100 |
| PHA | 20 | 1334.5 ± 158* |
| LPS | 25 | 3227 ± 177** |
| PQ$_2$A | 100 | 3002 ± 147** |
| PQ$_2$B | 100 | 947 ± 42** |
| PQ$_2$C | 100 | 186.5 ± 10.5* |
| PQ$_2$D | 100 | 201 ± 5** |
| CVT-E002 | 100 | 1395.5 ± 159.5* |
| PQ$_2$ | 100 | 2321.5 ± 8.5** |
| PQ$_{223}$ | 100 | 3237 ± 13** |

* and ** represent P < 0.05 and P < 0.01, respectively.
n = 3.

As the results indicate, the order of the potency is PQ$_{223}$>PQ$_2$>CVT-E002.

EXAMPLE 5

Chemical Determination of Total Carbohydrate and Protein Composition of CVT-E002, PQ$_1$, PQ$_2$, PQ$_3$, and PQ$_{223}$ Three batches of each fraction CVT-E002, PQ$_1$, PQ$_2$, PQ$_3$, and PQ$_{223}$ were obtained, and the total carbohydrate and protein composition were measured in each fraction. The total carbohydrate content was determined by the phenol-sulfuric method, as known in the art. The protein content was assayed by Lowry method, as known in the art, and bovine serum albumin was used as standard. The results are shown in the following Table.

TABLE 4

Comparison of Protein and Carbohydrate content of fractions

| Sample | Protein Content (%) | Total Carbohydrate (%) |
|---|---|---|
| E002-1 | 9.32 | 66.4 |
| E002-2 | 7.38 | 69.9 |
| E002-5 | 8.31 | 60 |
| PQ$_1$-24 | 2.6 | 90.3 |
| PQ$_1$-25 | 2.6 | 93.6 |
| PQ$_1$-27 | 2.9 | 96.1 |
| PQ$_2$-24 | 5.6 | 52.6 |
| PQ$_2$-25 | 5.4 | 46.8 |
| PQ$_2$-27 | 5.3 | 43.6 |
| PQ$_3$-24 | 7.9 | 52.6 |
| PQ$_3$-25 | 8.5 | 64.2 |
| PQ$_3$-27 | 7.1 | 68.0 |
| PQ$_{233}$-7 | 5.8 | 78.0 |
| PQ$_{233}$-8 | 2.8 | 81.0 |
| PQ$_{233}$-9 | 2.9 | 85.2 |

EXAMPLE 6

Chemical Determination of Monosaccharide Composition of CVT-E002, PQ$_1$, PQ$_2$, and PQ$_{223}$ Since total carbohydrate content mainly represented the amount of polysaccharides and oligosaccharides, the molar ratios of monosaccharides for certain fractions were also determined.

Lots of fractions CVT-E002, PQ$_1$, PQ$_2$ and PQ$_{223}$ were subjected to acid catalyzed hydrolysis to liberate their structural units, monosaccharides. A qualitative and quantitative analysis of the liberated monosaccharides was performed by HPLC after they were derivatized with MPP (3-methyl-1-phenyl-2-pyrazolin-5-one). The detailed methods are described as follows: a sample solution in 2 N HCl was heated at 95-100° C. for 6 h. The mixture was neutralized with NaOH solution. An internal standard was added. MeOH and aqueous NaOH solution (0.3 N) were then added to this mixture. This was then stirred at 50-60° C. for 8 hr (or at room temperature for one week). The mixture was diluted (1:10) with water, and analyzed by HPLC. The MPP-derivatized samples were analyzed with a C-18 column, with an eluent of 18% acetonitrile in 0.1 M phosphate buffer (pH 7), at a flow rate of 1 ml/min, UV detector at 245 nm. The following Table shows the molar ratio of monosaccharides of CVT-E002, PQ$_1$, PQ$_2$ and PQ$_{223}$. Trace amounts of glucuronic acid was found in some CVT-E002, PQ$_1$ and PQ$_2$ samples.

TABLE 5

Monosaccharide Composition of
CVT-E002, PQ$_1$, PQ$_2$ and PQ$_{223}$ (% in molar)

| Sample | Rhamnose | Galacturonic Acid | Glucose | Galactose | Arabinose |
|---|---|---|---|---|---|
| E002-1 | 2.8 | 17.9 | 53 | 13.3 | 13 |
| E002-2 | 1 | 13.1 | 56.7 | 12.7 | 15.2 |
| E002-3 | 2.9 | 20.4 | 42.1 | 16.5 | 16.3 |
| PQ$_1$-21 | 0.67 | 8.27 | 82.6 | 4.57 | 3.72 |
| PQ$_1$-22 | 0.48 | 6.38 | 85 | 4.56 | 3.55 |
| PQ$_1$-23 | 0.48 | 8.24 | 80.7 | 4.68 | 4.72 |
| PQ$_2$-22 | 3.6 | 45.1 | 15.4 | 19.8 | 16.2 |
| PQ$_2$-26 | 3.8 | 44.2 | 15.6 | 19 | 14.4 |
| PQ$_2$-27 | 3.8 | 44.2 | 15.6 | 19 | 14.4 |
| PQ$_2$-28 | 4 | 45.3 | 13.8 | 20.5 | 16.3 |
| PQ$_{223}$-7 | 5.5 | 40.8 | 4.1 | 28.2 | 20.3 |
| PQ$_{223}$-8 | 5.4 | 38.1 | 3.9 | 29.5 | 22.1 |
| PQ$_{223}$-9 | 5.4 | 36.7 | 5.4 | 28.8 | 22.7 |

As the result indicate, the order of glucose content is as follows: PQ1>CVT-E002>PQ2>PQ3; and the content of the galacturonic acid is as follows: PQ2>PQ223>CVT-E002>PQ1.

EXAMPLE 7

Immune Regulation of Ginseng Fractions

1. Macrophage activity

The effects of CVT-E002, PQ$_2$, G$_2$ and PQ$_{223}$ on murine macrophages were studied in vitro using peritoneal exudate macrophages from C57B1/6 mice which preferentially mount a cell-mediated response and Balb/c mice which preferentially mount an antibody-mediated response. IL-1, IL-6 and TNF-α production were measured after macrophages were stimulated with 100 μg/ml of test samples. The methods are described as follows.

A. Preparation of Macrophages from Peritoneal Exudate Cells and Cell supernatant.

1). 1 ml of 3% thioglycollate was injected into the murine peritoneal cavity and peritoneal exudate macrophages were harvested from the peritoneal cavity after 3 days.
2). Cell suspension was washed twice with Hanks buffer by centrifugation at 1100 rpm at 4° C. for 5 min.
3). Macrophages were suspended in RPMI-10% FBS medium.
4). Cells were counted and diluted to a final concentration of 10$^6$/ml with RPMI-10% FBC medium.

5). Macrophages were cultured in $10\times10^6/10$ ml RPMI-10% FBS at 37° C. for 2 hrs. Supernatant was discarded and the precipitated macrophages were washed with 10 ml of PBS twice.
6). Macrophages were harvested and re-suspended in RPMI-10% FBS.
7). Macrophage ($5\times10^5$) were cultured with 10 mg/ml of LPS or 100 mg/ml of test sample for 24 or 48 hrs, after which time the supernatants were collected and filter sterilized for the bioassay (IL-1, IL-6 and TNF-α). Experiments were carried out in triplicate.

B. IL-1 Determination in Supernatant.

The NOB1 cell line is a TK-variant of the EL4 cell line that generates CTLL growth stimulating activity (IL-2) in response to IL-1. Since NOB1 cells do not incorporate $^3$HTdR, a response to IL-1 can be measured in terms of uptake by the CTLL line. The procedure is described as follows.

1). $10^4$ CTLL cells were combined with $4\times10^4$ NOB1 cells in 200 µl of 5% FBS in IMDM in each well of a 96-well flat-bottom microtiter plate. Serially diluted IL-1 test samples of 4, 8, 16 or 32-fold or serial dilutions of IL-1 standards were applied. The final volume in each well was 200 µl. Each sample was prepared in triplicate.
2). Plates were incubated for 24 hr in a 37° C. 5% $CO_2$ humidified incubator.
3). [$^3$H]-thymidine was added for the last 5 hr of incubation.
4). Cells were harvested and [$^3$H]-thymidine incorporation was measured by liquid scintillation counting.
5). IL-1 concentration was calculated. The results are shown in the following Table.

TABLE 6

Effect of ginseng fractions on IL-1 production by murine macrophages

| Macrophages[1] stimulated with . . . | Production of IL-$1^2$ (pg/ml) |
|---|---|
| cells only | 15.7 ± 1.0 |
| LPS | 27.7 ± 1.9** |
| CVT-E002 | 18.1 ± 1.2* |
| $PQ_2$ | 19.5 ± 0.9* |
| $G_2$ | 17.7 ± 0.7* |
| $PQ_{223}$ | 19.9 ± 1.4* |

[1]Peritoneal exudate macrophages $5 \times 10^5$/ml were cultured with 100 µg/ml samples, 10 µg/ml LPS for 48 hrs and culture supernatant was harvested.
[2]Assay of IL-1 was performed using NOB1 and CTLL cell lines and results were expressed as mean ± SD
*P < 0.05;
**P < 0.01

The results show that CVT-E002, $PQ_2$, $G_2$ and $PQ_{223}$ significantly stimulated macrophages from C57B1/6 mice to produce IL-1. All test samples showed a similar potency of stimulating IL-1 production.

C. Determination of IL-6

The proliferation of a murine B cell hybridoma cell line, B9, is IL-6-dependent. B9 cells were cultured in a series of microwells containing decreasing concentration of the test samples. The procedure was as follows.

1). The number of B9 cells in an aliquot removed from the stock culture flask was counted at their log-phase of growth.
2). The cells were centrifuged for 5 min in a tabletop centrifuge at 180× g, 4° C., and the pellet was resuspended in 10 ml of complete RPMI-10 medium. The procedure was repeated twice and the cells were resuspended in complete RPMI-10 medium at $2\times10^3$ cells/ml.
3). 100 µl of washed cells ($2\times10^3$ cells/ml) was added to each well of a 96-well microtiter plate.
4). 100 µl of 2-fold serial dilutions of the test samples were added to each well, reserving two or three rows of the plate for IL-6 standards.
5). The plates were incubated for 72 hr in a humidified 37° C., 5% $CO_2$ incubator.
6). [$^3$H]-thymidine was added and plates were incubated for 4 hr at 37° C.
7). The cells were harvested and [$^3$H]-thymidine incorporation was determined using a liquid scintillation counter.
8). IL-6 concentration was calculated. The results are as shown in the following Table.

TABLE 7

Effect of ginseng on IL-6 production by murine macrophages

| Macrophages[1] stimulated with . . . | Production of IL-$6^2$ (pg/ml) | |
|---|---|---|
| | C57B1/6 mice | Balb/c mice |
| cells only | 71.7 ± 7 | 102 ± 1.8 |
| LPS | 14312.5 ± 269.4** | 22496.8 ± 2381.2** |
| CVT-E002 | 181.5 ± 2.1** | 185.5 ± 10* |
| $PQ_2$ | 219.3 ± 30.3** | 243.4 ± 6.4** |
| $PQ_{223}$ | 2058.3 ± 137.9** | 2387.2 ± 301.6** |

[1]Peritoneal exudate macrophages $5 \times 10^5$/ml were cultured with 100 µg/ml samples, 10 µg/ml LPS for 24 hrs and culture supernatant was harvested.
[2]Assay of IL-6 was performed using B9 cell line and results were expressed as mean ± SD
*P < 0.05;
**P < 0.01

CVT-E002, $PQ_2$ and $PQ_{223}$ increased the production of IL-6 in supernatant of macrophages from C57B1/6 and Balbic mice. The potency is $PQ_{223}>PQ_2>CVT$-E002.

D. Measurement of TNF-α

The following protocol employed TNF-sensitive, actinomycin D-treated murine L929 fibroblasts to quantify TNF activity in supernatants derived from cell cultures. 1). $4\times10^4$ L929 cells in 50 µl of IMDM-5% FSC were added into each well.
2). 50 µl of test sample was added to the second well of each row (column 2). Two-fold serial dilutions were made by gently mixing the contents of well 2 and transferring 50 µl from well 2 into well 3. The contents of well 3 were mixed gently, and 50 µl from well 3 was transferred into well 4. This procedure was continued through well 12. Finally, the contents of all wells in column 12 were gently mixed and 50 µl was discarded from each well. At this point, all wells contained 50 µl
3). 50 µl of actinomycin D solution was added to each well (2 µl ml).
4). The plates were incubated for 24 hr at 37° C. in 5% $CO_2$ in air.
5). 5 µl of Neutral Red was added to each well and the plates were incubated for 2.5 hours.
6). All supernatants in each well were quickly and carefully rinsed and emptied, and plates were washed with 200 µl of PBS twice.
7). The PBS was aspirated and 100 µl of 50% ethanol in 0.05M $NaH_2PO_4$ was added to each well and shaken for 5 min at room temperature.
8). Each well was read immediately with a microtiter plate reader at an absorbance of 570 nm.
9). TNF-α concentration was calculated. The results are shown in the following Table.

TABLE 8

Effect of ginseng on TNF-α production by murine macrophages

| Macrophages[1] stimulated with . . . | Production of TNF-α[2] (pg/ml) | |
|---|---|---|
| | C57B1/6 mice | Balb/c mice |
| cells only | 6.1 ± 1.9 | 4.8 ± 0.7 |
| LPS | 55.2 ± 1.6** | 71.4 ± 15.5** |
| CVT-E002 | 19.7 ± 2.5** | 17.9 ± 2.8** |
| $PQ_2$ | 3.5 ± 0.8 | 3.9 ± 0.2 |
| $G_2$ | 6.1 ± 1.2 | 7.2 ± 0.1* |
| $PQ_{223}$ | 16.9 ± 2.5** | 15.2 ± 2.2** |

[1]Peritoneal exudate macrophages 5 × 10⁵/ml were cultured with 100 μg/ml samples, 10 μg/ml LPS for 48 hrs and culture supernatant was harvested.
[2]Assay of TNF-α was performed using L929-8 cell line and results were expressed as mean ± SD of TNF-α production by macrophages.
*$P < 0.05$;
**$P < 0.01$ TNF-α production was induced by CVT-E002 and $PQ_{223}$ in supernatant of macrophages from Balb/c or C57B1/6 cell lines. TNF-α in the supernatant of macrophages from Balb/c mice was significantly stimulated by $G_2$. $PQ_2$ seemed not to stimulate TNF-α production by macrophages.

2. Serum Immunoglobulin Production

Serum immunoglobulin production (total IgG) increased 21% in mice fed with CVT-E002, 26% in mice fed with $PQ_2$ and 31% in mice fed with $PQ_{233}$, compared with mice fed with water. The potency is PQ223>PQ2>CVT-E002. Results are shown in Table 9.

TABLE 10

In vivo immunoglobulin production by mice (n = 15)

| Mice fed with . . . | IgG (μg/ml) ± SD |
|---|---|
| Water | 275.16 ± 32.34 |
| CVT-E002 | 333.01 ± 50.88* |
| $PQ_2$ | 346.81 ± 31.39** |
| $PQ_{223}$ | 400.46 ± 54.48** |

3. Specificity of Mitogenic Activity of $PQ_{223}$

Well known mitogens such as PHA or LPS show specificity as to the type of cells they stimulate. It is important to know which specific type of spleen cells are stimulated by ginseng fractions. We therefore separated T cells by an affinity column and enriched for B cells by T cell depletion.

A. T-Cell Enrichment

A single cell suspension of spleen cells was layered on lymphocyte-M (Cedarlane Labs) to remove red blood cells. The lymphocytes were then passed through an affinity chromatography column (Biotex Co. Ltd., Edmonton, Alberta) which removes B cells by adherence to the mouse immunoglobulin coated beads. The eluant consisted of an enriched population of T cells. Determination of the percentage of T cells relative to other cell types was done by the viability test using anti-thy 1.2 monoclonal antibody and complement treatment.

B. B-cell Enrichment

After removal of red blood cells from the spleen cell population, the lymphocytes were incubated with monoclonal anti-thy 1.2 antibody for one hour at 37° C. Low-tox rabbit complement was then added and incubated for half an hour at 4° C. This procedure depleted the cell suspension of T cells, resulting in an enriched B cell population.

C. Culturing with $PQ_{223}$

Figure 7:
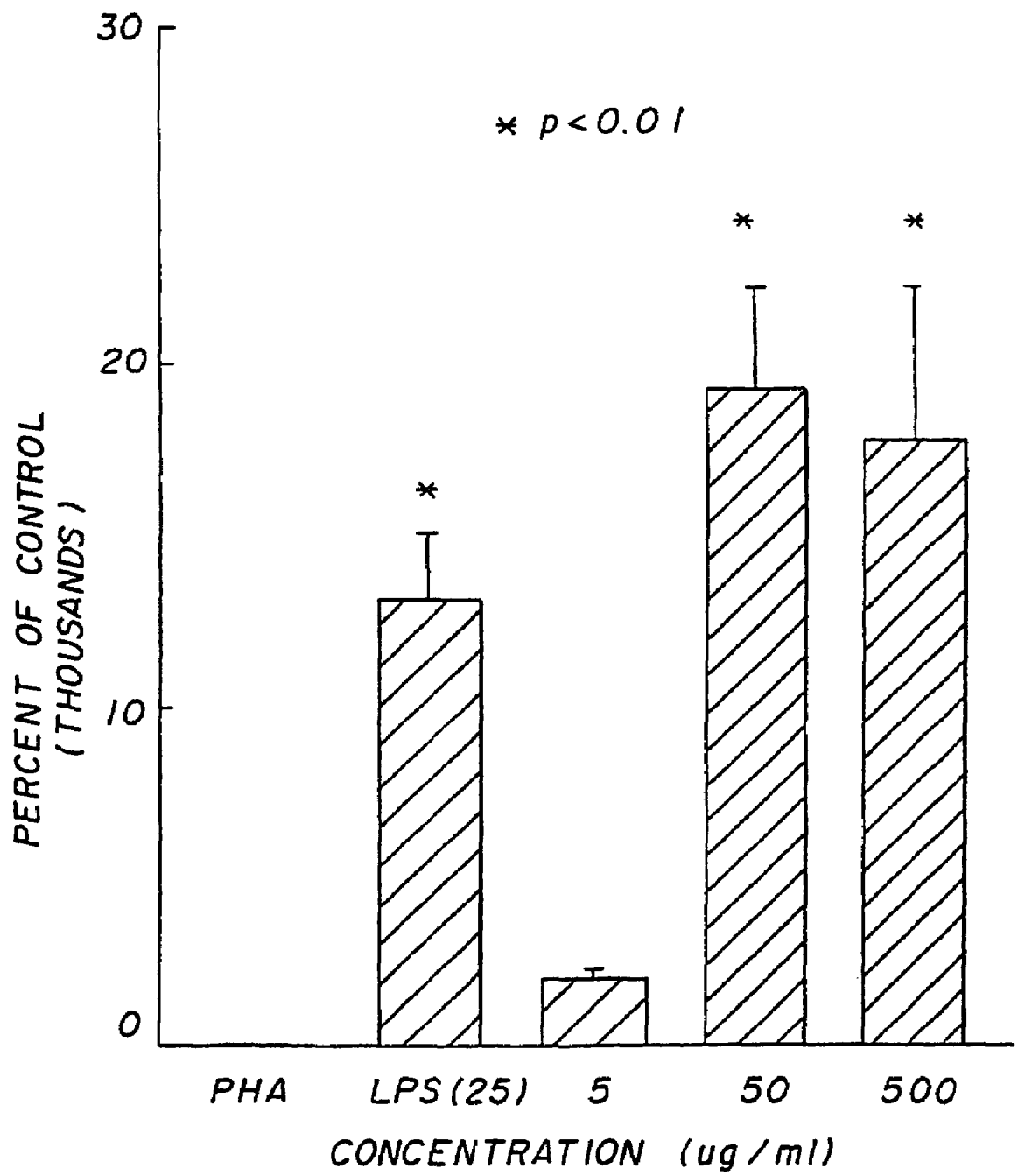
FIG. 7 shows the effect of ginseng fraction $PQ_{223}$ on mouse splenocyte B cell proliferation.
Figure 8:
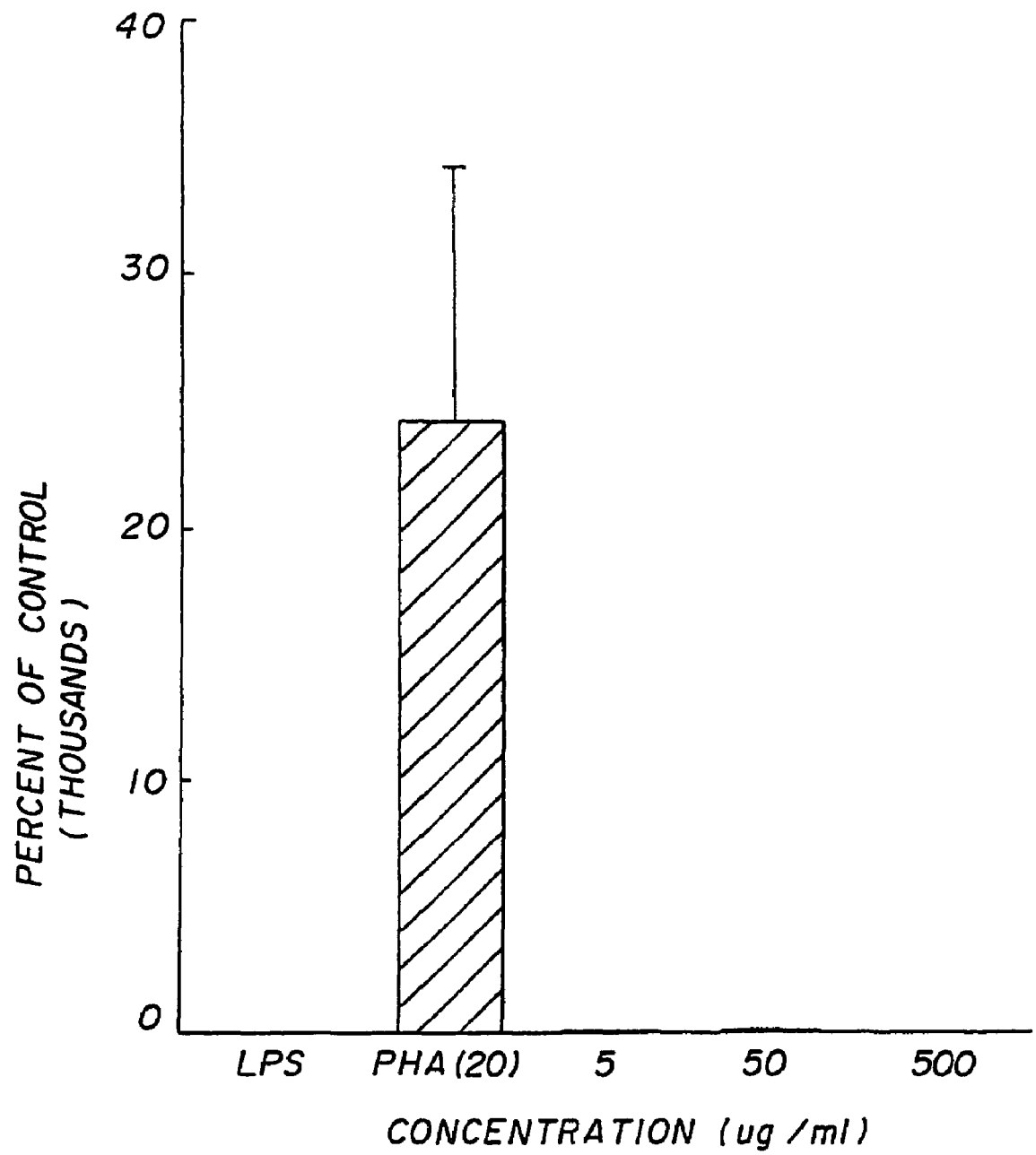
FIG. 8 shows the effect of ginseng fraction $PQ_{223}$ on mouse splenocyte T cell proliferation.
Figure 9:
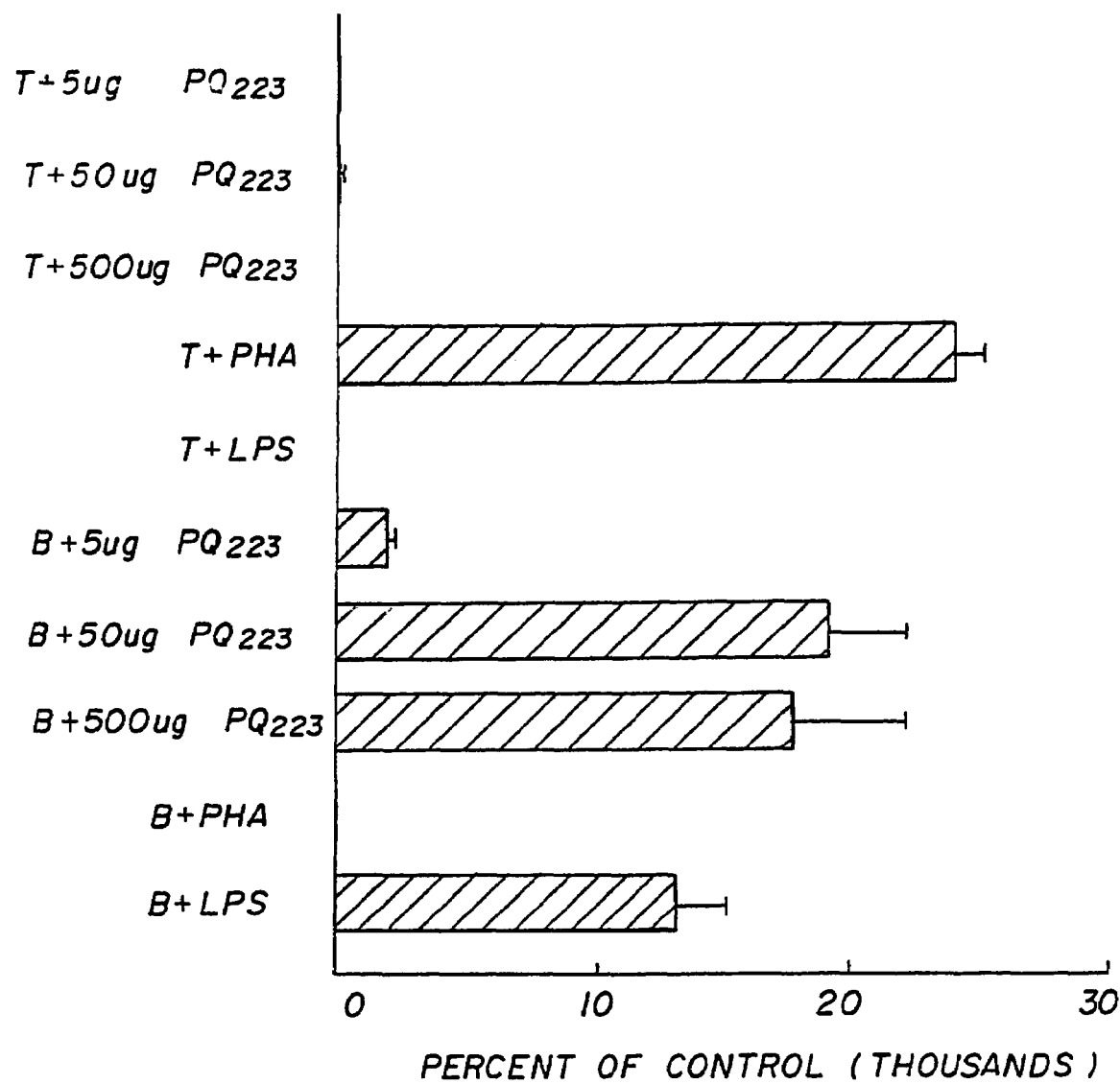
FIG. 9 shows the specificity of the effect of ginseng fraction $PQ_{223}$ on mouse splenocyte T and B cell proliferation.

B or T cells were cultured with varying doses of $PQ_{223}$, and the responses were measured in terms of tritiated thymidine incorporation. FIGS. 7 and 8 show the proliferation effect of $PQ_{223}$ on relatively purified B and T cells, respectively. Control groups included cells treated with LPS, a B cell-specific mitogen, and PHA, a T cell-specific mitogen. $PQ_{223}$ was found to be B cell-specific (see FIG. 9).

4. The Effect of $PQ_{223}$ on Antibody Production In Vitro

Spleen cells were cultured for 72 hours in the presence of varying doses of $PQ_{223}$. Control cultures consisted of a group to which 25 μg of LPS was added, and another to which no mitogen was added. The supernatants were tested for the presence of soluble immunoglobulins using the Enzyme Linked Immunosorbent Assay (ELISA). The supernatant containing soluble immunoglobulins was serially diluted in 0.1 M tris buffer (pH 9). Microtiter plates were coated with this supernatant and incubated at 4° C. overnight. The plates were washed with PBS Tween three times, then 100 μl of the antibody-enzyme conjugate Goat F(ab')2 anti-mouse Ig horseradish peroxidase (Tago Inc., Burlingame Calif.) was added at a 1:1000 dilution. The plate was incubated for one hour at room temperature. The plate was again washed three times with PBS, then 100 μl of ABTS peroxidase substrate (Kirkegaard and Perry Lab Inc.) was added to each well. One hour later absorbance was measured at a wavelength of 405 nm by a Flow Multiscan ELISA reader.

Figure 10:
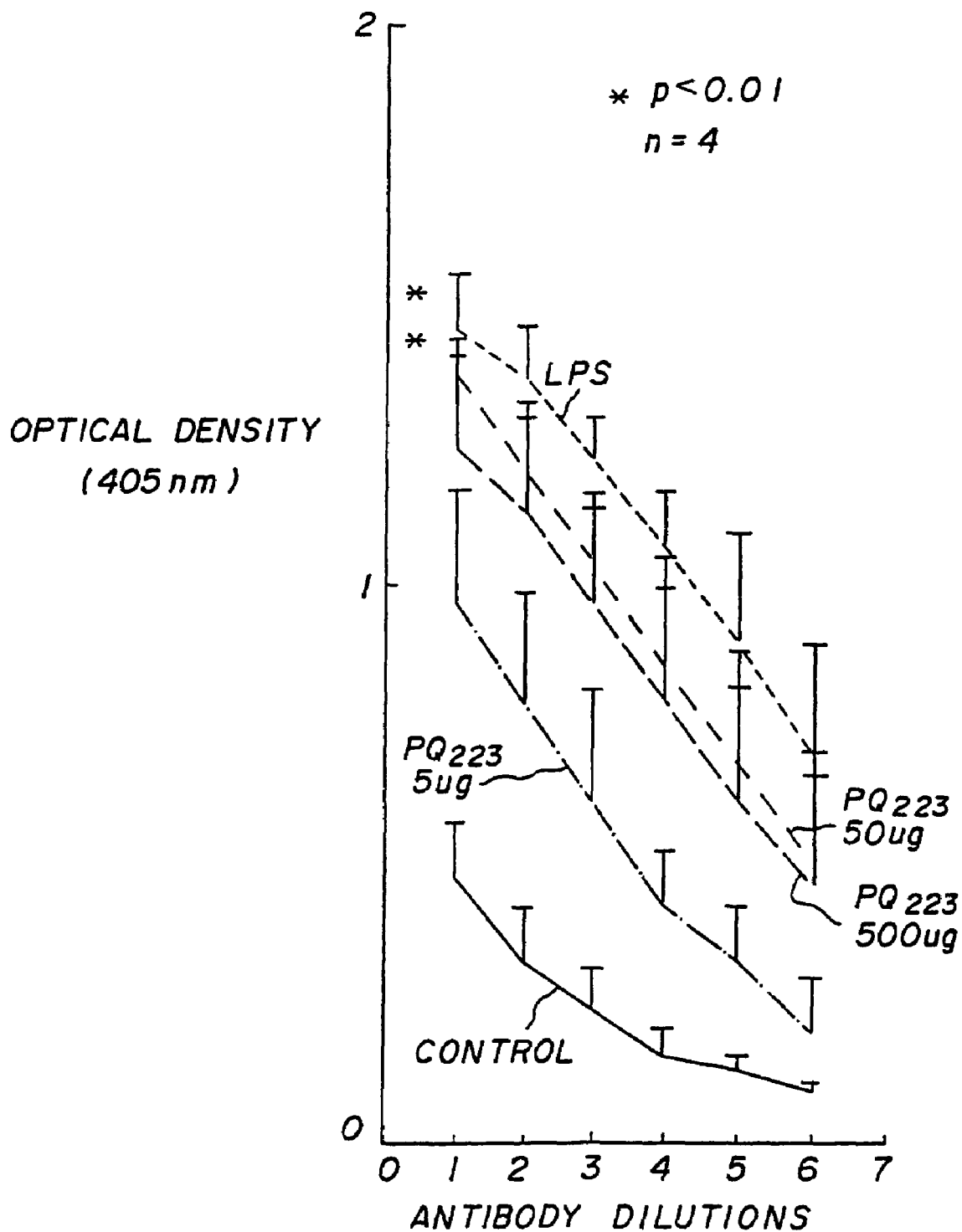
FIG. 10 shows the effect of ginseng fraction $PQ_{223}$ on in vitro antibody production by mouse spleen.

FIG. 10 shows that 50 μg/ml $PQ_{223}$ stimulated the production of immunoglobulins comparable to that of 25 μg LPS. A higher concentration of $PQ_{223}$, 500 μg/ml, did not elicit a higher degree of antibody production. This dose response curve is consistent with the proliferative responses of heterogeneous spleen cell population and purified B cells. These results were based on four experiments.

5. In Vivo Antibody Plaque Forming Cells

Figure 11:
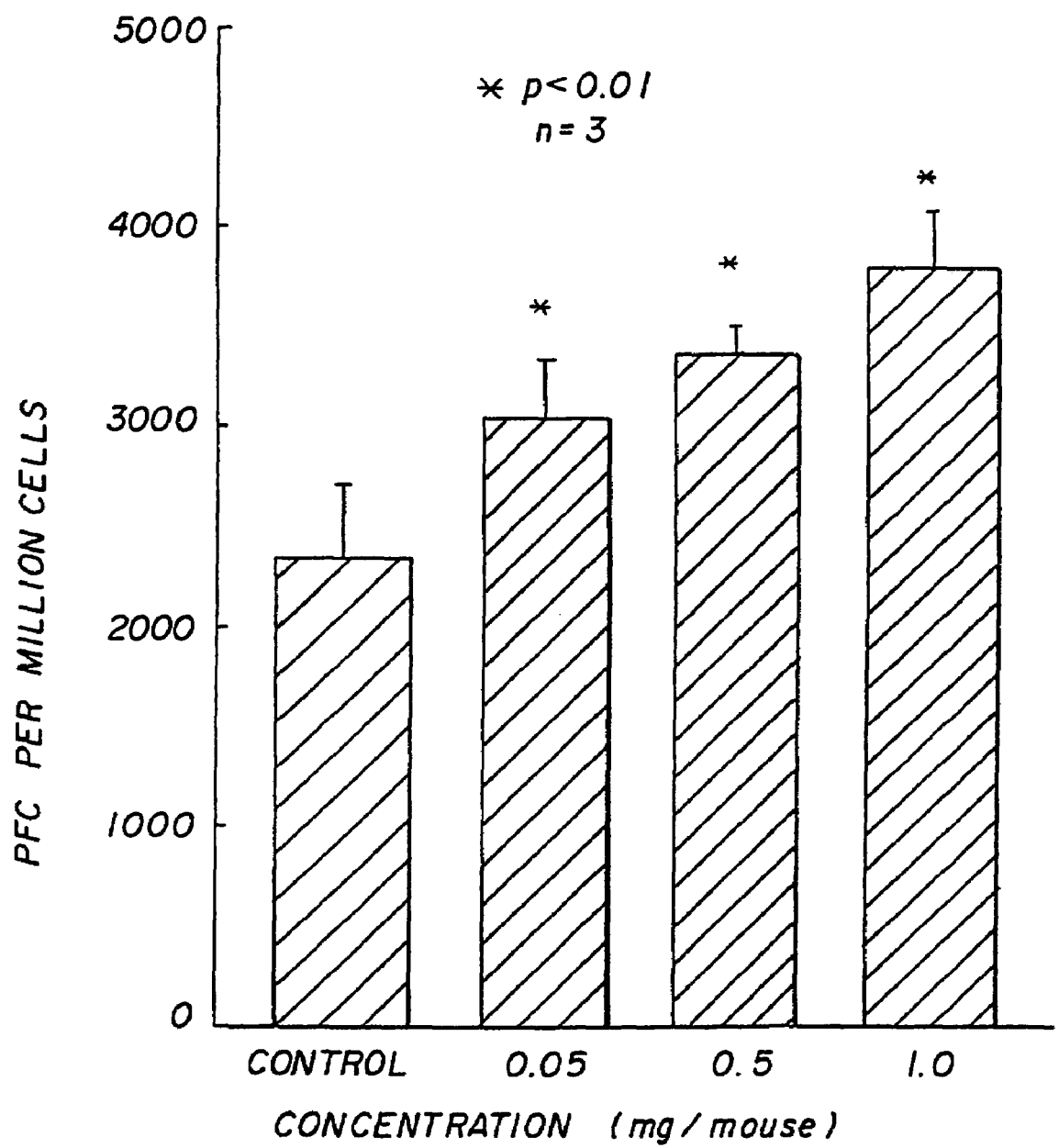
FIG. 11 shows the enhancement of plaque forming cells (PFC) in mice injected with ginseng fraction $PQ_{223}$.

Three concentrations of $PQ_{223}$ were i.v injected to three groups of 3 mice each. A control group was injected with a balanced salt solution. At the end of seven days of intravenous treatments with $PQ_{223}$, the mice were immunized with 0.2 ml of a 10% SRBC suspension in HBSS. Five days after immunization the mice were sacrificed and single cell suspensions from the spleens were prepared and adjusted to 4×10⁶ cells per ml. A 0.1 ml aliquot of this cell suspension was mixed with 0.3 ml of a 10% SRBC solution guinea pig complement and 0.5 ml RPMI medium. Seventy microliters of this mixture was transferred to a Cunningham chamber. The chamber was sealed with paraplast wax and was incubated at 37° C. for one hour prior to counting of plaque forming cells. All PFC levels are expressed as per one million spleen cells. FIG. 11 shows that all three doses significantly enhanced antibody production in mice injected with the compound.

In summary, the results of the present studies indicate that the ginseng fractions of the invention activate macrophages to produce cytokines such as IL-1, IL-6 and TNF-α. They also activate lymphocytes, particurlarly B-lymphocyte proliferation and antibody production. The overall humoral mediated immune system was stimulated indicating the preventive effects on infections. The reported action of TNF-α production includes antiviral and anti-tumor benefits. TNF-α has also been reported to be of therapeutic benefit in the treatment of a variety of parasitic infections.

The following citations referred to in the Background of the Invention are hereby incorportated by reference.
1. Tomoda et al. *Biol. Pharm. Bull.*, 16, 22-5 (1993).
2. Tomoda et al. *Biol. Pharm. Bull.*, 17, 1287-91 (1994).
3. Tomoda et al. *Biol. Pharm. Bull.*, 16, 1087-90 (1993).

4. Gao et al. *Planta Medica*, 55, 9-12 (1989).
5. Gao et al. *Carbohydr. Res.*, 181, 175-87 (1988).
6. Kiyohara et al. *Carbohydr. Res.*, 263, 89-101 (1994).
7. Shin et al. *Carbohydr. Res.*, 300, 239-49 (1997).
8. Yamada et al. *Phytotherapy Res*, 9, 264-9 (1995).
9. Konno et al. *Planta Medica*, 50, 434-6 (1984).
10. Hikino et al., unpublished.
11. Oshima et al. *J. Ethnopharmacology*, 14, 255-9 (1985).
12. Konno et al. *Int. J. Crude Drug Res.*, 25, 53-6 (1987).
13. Konno et al. *J. Ethnopharmacology*, 14, 69-74 (1985).
14. Oshima et al. *J. Natural Products*, 50, 188-90 (1987).
15. Lee et al. *Anticancer Res.*, 17, 323-32 (1997).
16. Kim et al. *Planta Medica*, 64, 110-5 (1998).
17. Miao et al. *Shengwu Huaxue ZaZhi*, 9, 610-4 (1993).
18. Ma et al. *Baiqiuen Yike Daxue Xuebao*, 23, 236-8 (1997).
19. Zhu et al. *Zhongguo Yaolixue Tongbao*, 13, 76-8 (1997).

The invention claimed is:

1. A process of preparing ginseng fraction $PQ_{223}$, the process comprising:
   (a) providing ginseng fraction $PQ_2$;
   (b) fractionating the ginseng fraction $PQ_2$ to produce a first elution fraction and a second elution fraction, wherein the first elution fraction corresponds to a carbohydrate peak observed between 35 and 50 ml of elution volume and the second elution fraction corresponds to a carbohydrate peak observed between 50 and 85 ml of elution volume, as determined by gel filtration chromatography using the following materials:
      (1) a chromatographic column containing a matrix of a spherical cross-linked co-polymer of allyl dextran and N,N'-methylenebisacrylamide, having a bed dimension of 16×600 mm, a bed volume of 120 ml, and a fractionation range (MW) of 5000 to 250,000 for globular proteins and 1000 to 80,000 for dextrans, and
      (2) an elution buffer of Tris-HCl containing 0.1 N HCl and 0.3 M NaCl at a pH of 7.0; and
   (c) isolating and combining the first elution fraction and the second elution fraction to produce ginseng fraction $P_{223}$.

2. The method of claim 1, wherein ginseng fraction $PQ_2$ is fractionated using gel filtration chromatography.

3. Ginseng fraction $PQ_{223}$, produced according to the process of claim 1.

4. A pharmaceutical composition, wherein said pharmaceutical composition comprises the ginseng fraction $PQ_{223}$ according to claim 3 and a pharmaceutically acceptable carrier.

5. A method of preparing a pharmaceutical composition suitable for treating a condition characterized by low immunity, wherein said method comprises combining an effective amount of the ginseng fraction $PQ_{223}$ according to claim 3 and, optionally, combining an effective amount of another medicament that is suitable for treating a condition characterized by low immunity, with at least one pharmaceutically acceptable excipient to produce a pharmaceutical composition suitable for treating a condition characterized by low immunity.

6. The method of claim 5, wherein the condition is selected from the group consisting of common cold, influenza, chronic fatigue syndrome, AIDS and cancer.

7. A method of stimulating the production of IL-1, IL-6 and/or TNF-α in cells, wherein said method comprises contacting said cells with an effective amount of the ginseng fraction $PQ_{223}$ according to claim 3.

8. A method of activating B-lymphocyte proliferation and antibody production resulting from said B-lymphocyte proliferation, wherein said method comprises administering to a subject in need thereof an effective amount of the ginseng fraction $PQ_{223}$ according to claim 3.

9. A method of treating a condition characterized by low immunity in a patient in need thereof, comprising administering to the patient an effective amount of a ginseng fraction $PQ_{223}$ according to claim 3.

10. The method of claim 9, wherein the condition is selected from the group consisting of common cold, influenza, chronic fatigue syndrome, AIDS and cancer.

11. A method for activating B-lymphocyte proliferation and antibody production there from, comprising administering an effective amount of the ginseng fraction $PQ_{223}$ according to claim 3 to a patient in need thereof.

* * * * *